US00PP17378P2

(12) United States Plant Patent
Larsen

(10) Patent No.: US PP17,378 P2
(45) Date of Patent: Jan. 23, 2007

(54) ***OSTEOSPERMUM* PLANT NAMED 'SUNNY SABRINA'**

(50) Latin Name: *Osteospermum ecklonis (DC) T. Norl.*
Varietal Denomination: Sunny Sabrina

(75) Inventor: Bjarne Nyholm Larsen, Odense N (DK)

(73) Assignee: Sunny Osteospermum APS, Odense N (DK)

( * ) Notice: Subject to any disclaimer, the term of this patent is extended or adjusted under 35 U.S.C. 154(b) by 0 days.

(21) Appl. No.: 11/234,147

(22) Filed: Sep. 26, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Foley & Lardner LLP

(57) ABSTRACT

A new distinct cultivar of *Osteospermum* plant named 'Sunny Sabrina', characterized by its single, daisy type composite inflorescenses with elliptic, acute, ligulate ray florets and tubular disc florets; light to dark purple disc florets, and light red-purple to red-purple ray florets with gray-orange undersides; dark green to yellow-green, large leaves; ovate to spatulate leaves with 6–8 small, acute lobes; and short peduncles, branches and compact bushy plant shape.

3 Drawing Sheets

Botanical designation: *Osteospermum ecklonis* (*DC*) *T. Norl.*
Variety denomination: 'Sunny Sabrina'.

BACKGROUND OF THE INVENTION

The present Invention relates to a new and distinct cultivar of *Osteospermum* plant, botanically known as *Osteospermum ecklonis* (*DC*) *T. Norl.,* commonly known as Cape Daisy, and hereinafter referred to by the variety denomination 'Sunny Sabrina'.

The new *Osteospermum* is a product of a plant breeding program conducted by the inventor, Bjarne Larsen, in Stige, Odense, Denmark. The objective of the breeding program was to develop a new *Osteospermum* variety with upright plant habit, compact growth habit, interesting inflorescence color, and good keeping quality.

The new *Osteospermum* originated from a planned crossing of two selected *Osteospermum* parent plants made by the inventor in 2002 in Stige, Odense, Denmark. The female or seed parent is an *Osteospermum ecklonis* (*DC*) *T. Norl.* cultivar designated '90.024.00' (unpatented). The male or pollen parent is an *Osteospermum ecklonis* (*DC*) *T. Norl.* cultivar designated '999' (unpatented). The new *Osteospermum* cultivar 'Sunny Sabrina' was selected by the inventor as a single flowering plant within the progeny of the above cross in 2003 in a controlled environment in Stige, Odense, Denmark.

Asexual reproduction of the new *Osteospermum* cultivar by apical stem cuttings was first performed in February 2003 in Stige, Odense, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be unique characteristics of 'Sunny Sabrina'. These characteristics in combination distinguish 'Sunny Sabrina' as a new and distinct cultivar:

1. Single, daisy type composite inflorescenses with elliptic, acute, ligulate, flat, lanceolate ray florets and tubular disc florets;
2. Light to dark purple disc florets, and light red-purple to red-purple ray florets with gray-orange stripes on undersides;
3. Dark green to yellow-green, large leaves;
4. Ovate to spatulate leaves with 6–8 small, acute lobes; and
5. Short peduncles, branches and a compact bushy plant shape.

Plants of the parental cultivars, '90.024.00' (unpatented) and '999' (unpatented) are unavailable to provide a detailed botanical comparison to plants of the new cultivar 'Sunny Sabrina'.

Of the many commercial cultivars known to the present inventor, the most similar in comparison to the new *Osteospermum* cultivar 'Sunny Sabrina' is *Osteospermum* cultivar 'Sunny Silvia' (patented, U.S. Plant Pat. No. 10,354). In side-by-side comparisons conducted in Stige, Denmark, plants of 'Sunny Sabrina' differed from plants of 'Sunny Silvia' in the characteristics described in Table 1:

TABLE 1

| Trait | New Cultivar 'Sunny Sabrina' | Comparison Cultivar 'Sunny Silvia' (patented) |
|---|---|---|
| Plant height | About 20 cm | About 32 cm |
| Plant diameter | About 21 cm | About 48 cm |
| Number of Lateral Branches | Primary: 4<br>Secondary: 17 (flowering) | Primary: 6<br>Secondary: 25 |
| Lateral Branch Length | Primary: 3 cm<br>Secondary: 12–14 cm (incl. inflorescence) | Primary: 33 cm<br>Secondary: 9–12 cm |

TABLE 1-continued

| Trait | New Cultivar 'Sunny Sabrina' | Comparison Cultivar 'Sunny Silvia' (patented) |
|---|---|---|
| Lateral Branch Diameter | 4–5 mm | 6–7 mm |
| Internode Length | About 30 mm | 15–29 mm |
| Shape of Leaves | Ovate to spatulate, 6–8 acute lobes | Obovate, sinuate with 3–6 pointed lobes |
| Apex Shape of Leaves | Subacute | Acuminate |
| Size of Leaves | Length: 3–4 cm Width: 1–3 cm | Length: About 9 cm Width: About 3.5 cm |
| Mature Leaf Color | Upper side: RHS 139B Under side: RHS 147A | Upper side: RHS 147A Under side: RHS 147A |
| Venation Pattern | Brochidodromus, form of pinnate | Palmate |
| Petiole Length: | 10–20 mm | 35 mm |
| Inflorescence Height | 6–7 cm | 9 cm |
| Bud Color | From yellow-green, RHS 146C (base) to RHS 146B | Yellow-green, RHS 154A |
| Ray Floret Color (fully opened) | Upper side: Apex tip, RHS 72C, red-purple, with base, RHS 73D, light red-purple Under side: Gray-orange, RHS 176A, longitudinal stripes | Upper side: Purple, RHS 78B to white, RHS 155A on the sides Under side: Light violet, RHS 84D with stripes of RHS 84A |
| Ray Floret Color Fading | No fading; withering | Fading to nearly white at proximal end |
| Peduncle Length | About 5–9 cm | About 19 cm |

BRIEF DESCRIPTION OF THE PHOTOGRAPHS

The accompanying colored photographs illustrate the overall appearance of the new *Osteospermum* cultivar 'Sunny Sabrina' showing the colors as true as is reasonably possible with colored reproductions of this type. Colors in the photographs may differ slightly from the color values cited in the detailed botanical description which accurately describe the color of the new *Osteospermum* cultivar 'Sunny Sabrina'.

DETAILED BOTANICAL DESCRIPTION

Figure 1:
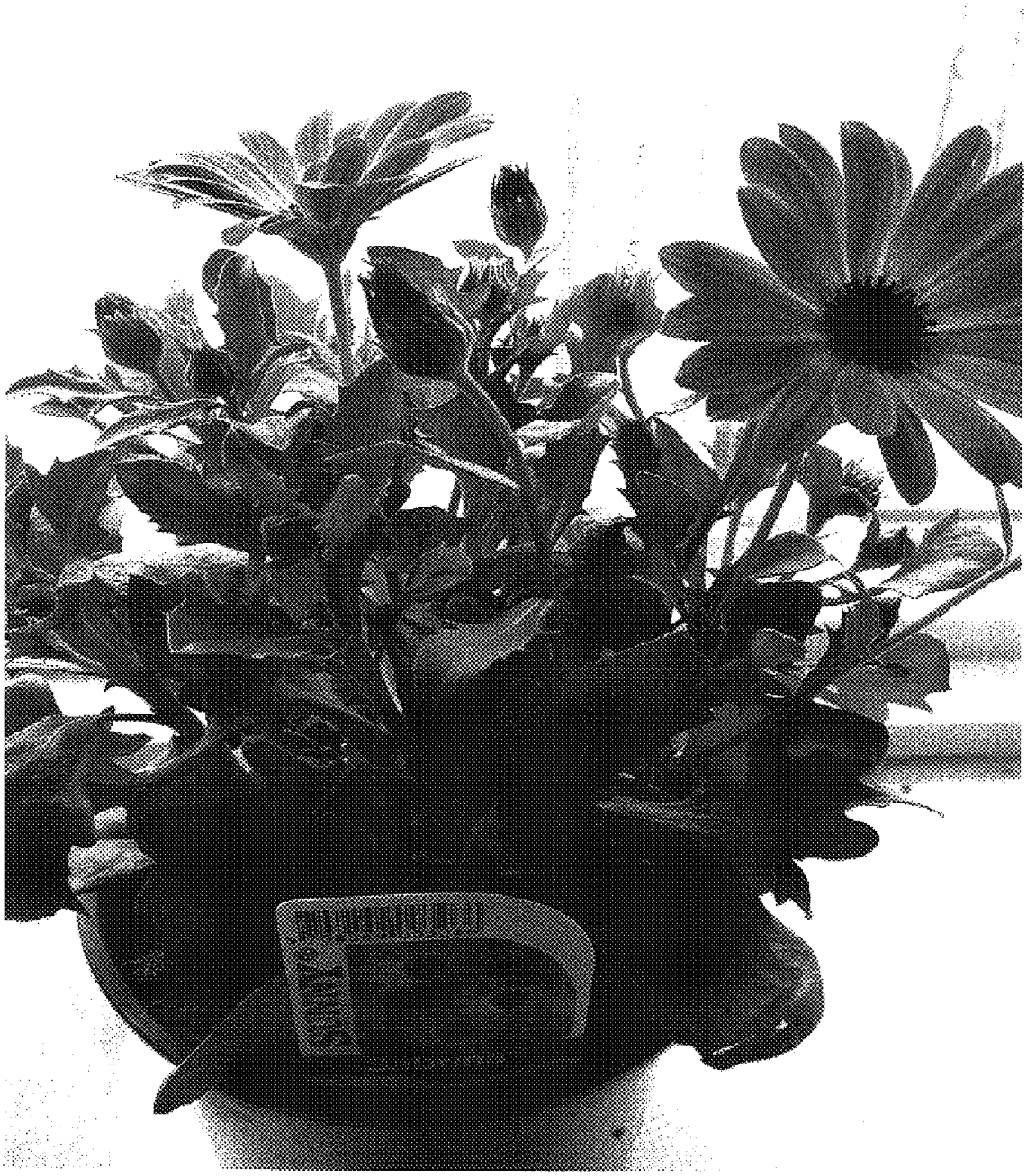
FIG. 1 shows a side perspective view of a typical potted flowering plant of 'Sunny Sabrina', as a produced cultivar, 20 weeks after planting.
Figure 2:
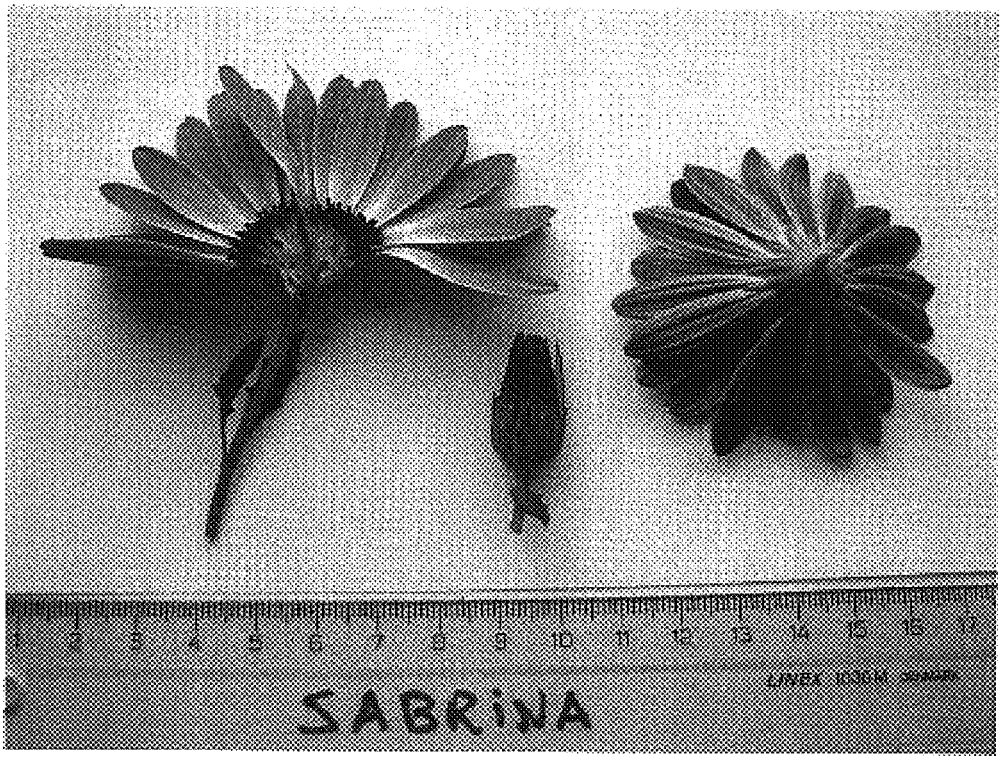
FIG. 2 shows a top and bottom view of a typical bud and inflorescence and of 'Sunny Sabrina', as a produced cultivar, 20 weeks after planting.
Figure 3:
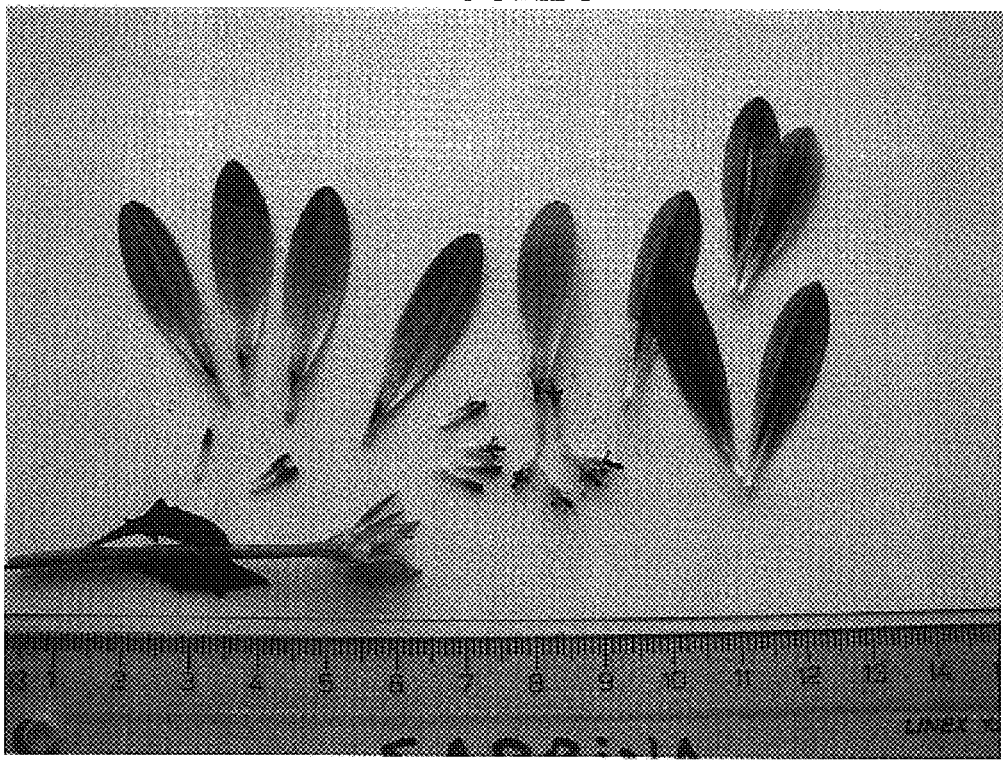
FIG. 3 shows a dissected view of a typical inflorescence of 'Sunny Sabrina', as a produced cultivar, 20 weeks after planting.
Figure 4:
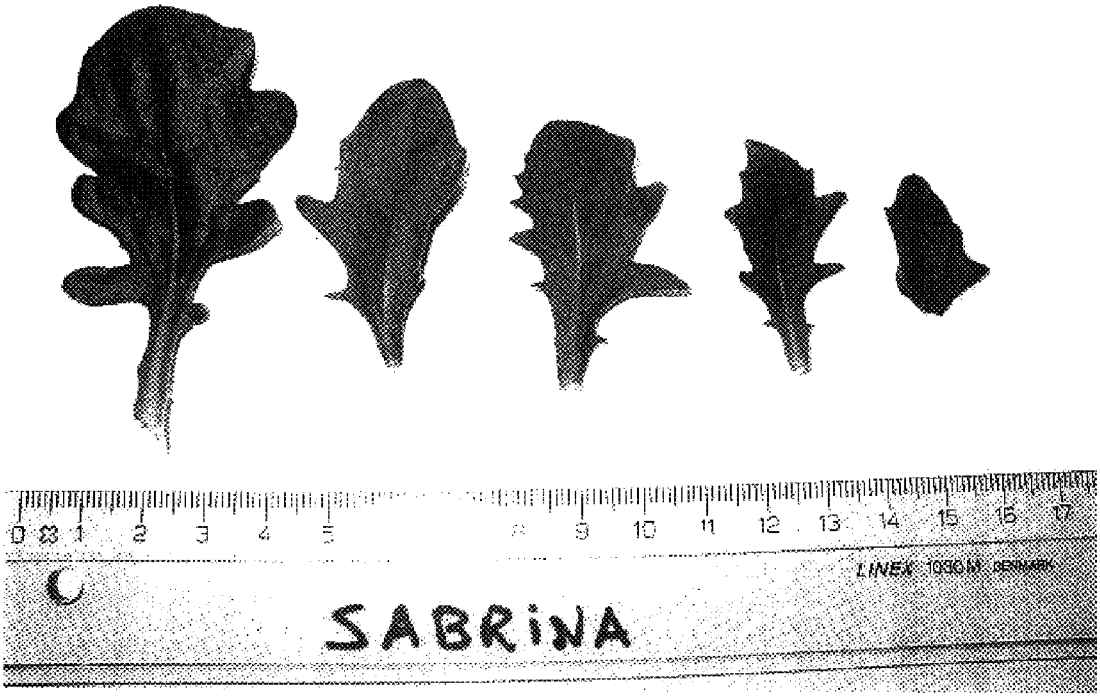
FIG. 4 shows a view of the leaves of a typical potted flowering plant of 'Sunny Sabrina', as a produced cultivar, 20 weeks after planting.

The new *Osteospermum* cultivar 'Sunny Sabrina' has not been observed under all possible environmental conditions. The phenotype of the new cultivar may vary with variations in environment such as temperature, light intensity, and day-length, without any change in the genotype of the plant.

The aforementioned photographs, together with the following observations, measurements and values describe plants of the new *Osteospermum* cultivar 'Sunny Sabrina' as grown in a greenhouse in Stige, Denmark, under conditions which closely approximate those generally used in commercial practice. Vegetative propagation with apical tip cuttings (4–5 leaves) took place in a greenhouse with propagation tents for 3 weeks with the day and night temperature averaging 20° C. day. The temperature was then lowered to the day and night temperature averaging about 14° C. The plants were subirrigated with a nutrient solution of 2–3 mS when needed and given supplementary irradiation with SON T lamps having an installed energy level of 400 $Wm^2$.

Color references are made to The Royal Horticultural Society Colour Chart (R.H.S.), $4^{th}$ edition 2000, except where general colors of ordinary significance are used. The photographs and descriptions were taken during the spring when outdoor day temperatures ranged from 7° C. to 15° C. and outdoor night temperatures ranged from 2° C. to 8° C. The age of the plants described is 20 weeks.

Botanical classification: *Osteospermum ecklonis* (*DC*) *T. Norl.*

Parentage:

*Female or seed parent.*—*Osteospermum ecklonis* (*DC*) *T. Norl.* designated '90.024.00' (unpatented).

*Male or pollen parent.*—*Osteospermum ecklonis* (*DC*) *T. Norl.* designated '999' (unpatented).

Propogation:

*Type.*—Apical stem cutting.

*Time and temperature to initiate roots.*—Summer: About 12 to 14 days at 20° C. to 22° C. in tunnels in a greenhouse. Winter: About 17 to 20 days at 20° C. to 22° C. in tunnels in a greenhouse.

*Time and temperature to develop roots.*—Summer: About 14 to 18 days at 20° C. to 22° C. in tunnels in a greenhouse. Winter: About 20 to 22 days at 20° C. to 22° C. in tunnels in a greenhouse.

*Rooting description.*—100% rooting.

*Rooting habit.*—Fine, fibrous and branching.

*Root color.*—RHS 155B, white.

Plant description:

*General appearance and form.*—Perennial plant with upright, inverse conical plant habit, and used as a potted or bedding plant. *Osteospermum* inflorescences in composite heads, daisy type.

*Growth and branching habit.*—Freely branching with lateral flowering branches forming at every node; dense and bushy. Basal branching and pinching required.

*Growth rate/vigor.*—Vigorous.

*Plant height* (*soil level to top of plant plant*).—About 20 cm.

*Plant width* (*spread*).—About 21 cm, Range: 20–22 cm.

*Plant strength.*—Low temperature tolerance to +1° C. High temperature tolerance: Not tested over 30° C., but flowering ceases over 28° C.

*Crop time to produce a mature flowering plant.*—After rooting, about 20 weeks are required to produce finished flowering plants in 11 cm pots.

Branches:

*Number of branches per plant.*—4 primary, 17 secondary.

*Length.*—Primary: About 3 cm. Secondary: 12–14 cm (including inflorescence).

*Diameter.*—About 4–5 mm.

*Internode length.*—About 30 mm.

*Strength.*—Strong.

*Aspect.*—Upright, branches at 70° angle.

*Texture.*—Glabrous.

*Color.*—RHS 144C, yellow-green.

Foliage description:

*Arrangement.*—Alternate (5 whorl), single, lobed, ovate to spatulate.

*Quantity of leaves per lateral branch.*—About 15–18.

*Length.*—About 3–4 cm.

*Width.*—About 1–3 cm.

*Overall shape of leaf.*—Ovate to spatulate, 6–8 acute lobes.

*Shape at apex.*—Mature leaf: Subacute. Young leaf: Acute.

*Shape at base.*—Attenuate to decussate.

*Margin.*—Entire, lobed (6–8 small, triangular lobes).

*Texture.*—Matte, scattered, short stiff hairs along veins and edges.

*Color of developing foliage.*—Upper surface: RHS 147A, yellow-green. Lower surface: RHS 148C, yellow-green.

*Color of mature foliage.*—Upper surface: RHS 139A, yellow-green. Lower surface: RHS 147A, yellow-green.

*Venation pattern.*—Brochidodromus, form of pinnate.

*Venation color.*—Only central vein discernible from leaf color: RHS 144A, yellow-green or RHS 147C.

*Petiole length.*—About 10–20 mm.

*Petiole diameter.*—About 2–4 mm (flat, winged).

*Petiole texture.*—Upper surface: Glabrous. Lower surface: Hirsute with scattered stiff hairs.

*Petiole color.*—Upper surface: RHS 145B, yellow-green. Lower surface: RHS 143A, yellow-green.

Inflorescence description:

*Appearance.*—Terminal and axillary inflorescences held above and beyond the foliage. Single, composite inflorescence form, radially symmetrical, with ligulate, flat, lanceolate-shaped ray florets and tubular disc florets massed at the center; ray and disc florets arranged acropetally on a capitulum. Inflorescences face upright with aspect of 80°.

*Natural flowering season.*—Continuous throughout the spring and summer in temperature regions. Season can be extended by vernalization and long day treatments. Flowering may cease if temperatures exceed 28° C.

*Time to flower.*—5 to 11 days (longevity of individual inflorescences is dependent on temperature and light conditions).

*Postproduction longevity.*—Inflorescences maintain good color and substance for about 14 days on the plant when grown in an outdoor environment. Inflorescences persistent, but wither to insignificance.

*Quantity of inflorescences.*—Freely flowering; more than 25 open inflorescences and inflorescence buds per plant.

*Fragrance.*—Flowers have a weak, fresh lemon scent.

Bud:

*Rate of opening (from showing color to fully open inflorescence).*—4 to 5 days.

*Quantity of buds per lateral stem.*—About 8.

*Length.*—About 0 to 12 mm at color showing.

*Diameter.*—About 0 to 10 mm.

*Shape.*—Globular until color, then ovoid.

*Color.*—From RHS 146C, yellow-green (base) to RHS 146B.

Peduncle:

*Length.*—Terminal: About 9 cm. Secondary: About 6 cm. Tertiary: About 5 cm.

*Diameter.*—About 2 mm.

*Appearance and angle.*—Terminal: Erect. Secondary: About 10 to 25 degrees from vertical. Tertiary: About 30 to 45 degrees from vertical.

*Strength.*—Strong.

*Texture.*—Glabrous.

*Color.*—RHS 144C, yellow-green.

Inflorescence:

*Inflorescence depth (height).*—About 6–7 cm.

*Inflorescence diameter.*—About up to 8 cm.

*Receptacle diameter.*—About 2 cm.

*Receptacle height.*—About ½ cm.

*Receptacle shape.*—Semiglobular.

*Receptacle color.*—RHS 145B, yellow-green.

Ray florets:

*Quantity per inflorescence.*—Typical number: 23. Observed number: 22–24.

*Length.*—About 30 mm, Range 28–32 mm.

*Width.*—About 9 mm.

*Overall shape.*—Elliptic ligulate, (flat, lanceolate).

*Shape at apex.*—Acute.

*Shape at base.*—Attenuate.

*Margin.*—Entire.

*Texture.*—Upper surface: Silky. Lower surface: Smooth.

*Orientation.*—Initially 45 degrees from vertical, with development, close to 80 degrees from vertical.

*Color (when opening).*—Ray: Upper surface: Apex, RHS N79A, dark purple. Lower surface: center stripe RHS 186B, gray-purple, stripes of RHS 82B, gray-red, few spots and edges RHS 179C, grayed red.

*Color (when fully opened).*—Upper surface: Apex tip RHS 72C, red-purple, base RHS 73D, light red-purple. Lower surface: Stripes now more gray-orange RHS 176A.

Disc florets:

*Quantity per inflorescence.*—Typical number: 70. Observed number: 60–80.

*Length.*—About 7–8 mm.

*Width.*—At apex: About 3 mm. At base: About 1 mm.

*Disc area diameter.*—About 14 mm.

*Overall shape.*—Tubular.

*Shape at apex.*—Star.

*Shape at base.*—Tube.

*Margin.*—Entire.

*Texture.*—Shiny, translucent.

*Color (when opening).*—Upper side: Apex, RHS N79A, dark purple, Under side: RHS 76D, light purple.

*Color (fully opened).*—Apex, RHS 183A, gray-purple; basal tube, RHS 76D, light purple.

Phyllaries:

*Quantity per inflorescence.*—About 18 in a single whorl.

*Length.*—About 6–12 mm.

*Width.*—About 1–3 mm.

*Overall shape.*—Lanceolate.

*Shape at apex.*—Acuminate.

*Shape at base.*—Fused.

*Margin.*—Entire.

*Texture.*—Upper surface: Glabrous. Lower surface: Slightly hirsute.

*Color.*—Upper surface: RHS 144D, yellow-green. Lower surface: RHS 144C, yellow-green.

Reproductive organs:

Androecium: On disc florets only.

*Stamen number.*—5 per floret; fused around style.
*Stamen length.*—About 6 mm.
*Anther shape.*—Linear.
*Anther length.*—About 2 mm.
*Anther color.*—RHS 79B, purple.
*Pollen amount.*—Abundant.
*Pollen color.*—RHS N25A, orange.

Gynoecium: On ray and disc florets.
*Quantity.*—1 per floret.
*Pistil length.*—About 4 mm.
*Stigma shape.*—Brush-like.
*Stigma color.*—RHS N187A, purple.
*Style length.*—About 3 mm.
*Style color.*—RHS N155D, white.
*Ovary color.*—RHS 1D, green-yellow.

Seed: None observed.
Fruit: None observed.
Disease/pest resistance: Good.
Disease/pest susceptibility: No pests or diseases observed.
Temperature tolerance: Plants of the new *Osteospermum* have exhibited good tolerance to draught, rain and wind; however, flowering may cease during hot periods (temperatures about 28° C.). Low temperature tolerance to 1° C.
Growth retardant(s): 3 times 0.2% Chlormequat drench during production.

I claim:

1. A new and distinct cultivar of *Osteospermum* plant named 'Sunny Sabrina', as illustrated and described herein.

* * * * *